United States Patent [19]

Perekalin et al.

[11] 3,947,492
[45] Mar. 30, 1976

[54] PROCESS FOR PRODUCING β-PHENYL-γ-AMINO BUTYRIC ACID HYDROCHLORIDE

[76] Inventors: Vsevolod Vasilievich Perekalin, ulitsa Voskova, 2, kv. 5; Alexandra Semenovna Sopova, ulitsa Varshavskaya, 73, kv. 64; Maiva Mikhailovna Zobacheva, ulitsa Vasi Alexeeva, 9, kv. 30, all of Leningrad; Rasma Yanovna Spunde, ulitsa Lenina, 2, kv. 51, Rizhsky Raion, Olaine; Uldis Yanovich Mikstais, ulitsa Lenina, 17, kv. 21, Rizhskv Raion, Olaine; Maiya Petrovna Silaya, ulitsa Mendeleeva 20, kv. 48, Rizhskv Raion, Olaine, all of U.S.S.R.

[22] Filed: Apr. 9, 1973

[21] Appl. No.: 349,672

[52] U.S. Cl..... 260/518 R; 260/326.45; 260/471 A; 424/319
[51] Int. Cl.² ................. C07C 99/00; C07C 99/06
[58] Field of Search .................. 260/518 R, 326.45

[56] References Cited
UNITED STATES PATENTS 3,634,428   1/1972   Keberle et al. ................ 260/471 A Primary Examiner—Richard L. Raymond
Attorney, Agent, or Firm—Waters, Schwartz & Nissen

[57] ABSTRACT

The invention relates to a new substance, namely the hydrochloride of β-phenyl-γ-aminobutyric acid of the following formula:

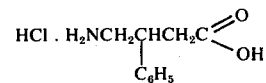

and to the process for its production which comprises condensing malonic ester with β-nitrostyrene resulting in the separation of an ester of γ-carbomethoxy-β-phenyl-γ-nitrobutyric acid at a temperature ranging from 0° to 14°C, reducing the ester thus obtained with hydrogen in the presence of the Raney nickel under a pressure of 6 to 30 atm, treating 3-carbomethoxy-4-phenyl-2-pyrrolidone, as formed by the reduction, with hydrochloric acid, and separating the desired product.

1 Claim, No Drawings

PROCESS FOR PRODUCING β-PHENYL-ν-AMINO BUTYRIC ACID HYDROCHLORIDE

The present invention relates to a new substance namely the hydrochloride of β-phenyl-γ-aminobutyric acid, and to a process for producing same.

The substance according to the invention has the following formula:

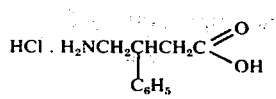

The novel compound is a white or a white with a slightly yellowish tint crystalline powder which is easily soluble in water, soluble to a lesser degree in alcohol, acetone, and practically insoluble in ether.

The hydrochloride of β-phenyl-γ-amino butyric acid possesses a pharmacological activity and is used in medicine as a drug having a calming or sedative effect on various neurotic and psychopathic states, enhancing the effect of soporific and neuropsychotropic agents.

Non-toxicity is the most important feature of hydrochloride of β-phenyl-γ-amino butyric acid, as by its chemical composition it approximates the products of the natural metabolism of the brain. Therefore, it can be used for calming excessively irritable children, middle-aged persons and to relieving nervous tension of healthy persons.

According to the invention, the process for the production of hydrochloride of β-phenyl-γ-amino butyric acid comprises condensing malonic ester with β-nitrostyrene resulting in the separation of the ester of α-carbomethoxy-β-phenyl-γ-nitrobutyric acid at a temperature of 0° to 14°C followed by reducing with hydrogen said condensation product in the presence of Raney nickel at a pressure of 6 to 30 atm, treating with hydrochloric acid the 3-carbomethoxy-4-phenyl-2-pyrrolidone formed as a result of said reduction, and separating the desired product from the solution.

The proposed process for the production of hydrochloride of β-phenyl-γ-amino butyric acid is conducted as follows.

The condensation of malonic ester with β-nitrostyrene is effected in a methanol solution in the presence of sodium methylate at a temperature of 0° to 14°C by intermixing and simultaneous cooling with ice.

In 30 minutes the reaction mixture is poured into diluted hydrochloric acid with ice. After drying in the open air, the separated crystalline product is suitable for further reprocessing without purification.

Then, the condensation product is hydrogenated in methyl alcohol in the presence of Raney nickel under a pressure of 5 to 30atm. 1.5 to 2 hours after the reduction is over, the solution is drained from the catalyst, which is washed three times with ethyl alcohol. The whole solution thus obtained is evaporated under vacuum prior to crystallization.

The reduction yields 3-carbomethoxy-4-phenyl-2-pyrrolidone which is subjected to hydrolysis without preliminary purification.

To this end, it is boiled in diluted hydrochloric acid for a period of no less than 6 hours. After adding activated charcoal to the obtained colored solution, it is again boiled for 15 min and filtered through a glass fabric.

The hydrochloride of β-phenyl-γ-amino butyric acid is separated through concentration by evaporation prior to crystallization. Then the salt is recrystallized from concentrated hydrochloric acid and dried at a temperature of 80°C. The purified and dry product is not hygroscopic.

The hydrochloride of β-phenyl-γ-aminobutyric acid is stable in storage and does not lose its pharmacological activity.

The nature of the present invention will become more fully apparent from a consideration of the following examples illustrative of the production of the hydrochloride of β-phenyl-γ-aminobutyric acid.

Example I 124.2 g of metallic sodium mixed with 990 ml of malonic ester and 2,700 ml of methyl alcohol are dissolved in a 20 l reactor provided with a mechanical stirrer, a thermometer, a separatory funnel and a coil. Added to the solution thus obtained during intermixing at a temperature of 10°C is a solution of 810 g of β-nitrostyrene in 9,000 ml of methyl alcohol. After 30 min, the reaction mixture is poured into a mixture composed of 495 ml of concentrated hydrochloric acid, 8 l of water and 10 kg of ice. After several hours, the separated thick oil solidifies into a dense mass which is comminuted and dried in the open air. The melting point of the methyl ester of α-carbomethoxy β-phenyl-γ-nitrobutyric acid is 60°C; the yield is 1,380 g.

The product thus obtained is reduced without purification in the following manner: on having been dissolved in 9,000 ml. of ethyl alcohol, it is placed together with 180 g of Raney nickel into an autoclave. The reaction mixture is purged with nitrogen, and hydrogen is passed therethrough. The reduction process is completed in 1.5 hrs at a pressure of 30 atm. The mixture is cooled. On draining the solution from the catalyst, the latter is washed three times with ethyl alcohol taken in portions of 750 ml each. The ethyl alcohol is decanted and added to the main solution. The ethyl alcohol is distilled off in vacuo to a volume of no less than 2,000 ml, the rest being crystallized. The yield of green 3-carbomethoxy-4-phenyl-2-pyrrolidone is 787 g. Without purification, it is boiled for a period of no less than 6 hrs with 1,500 ml of concentrated hydrochloric acid in 1,500 ml of water. The entire deposit is gradually dissolved. The completeness of hydrolysis is checked by taking off a 5 ml sample which is concentrated by evaporation to a dry substance. 0.5 g of dry substance should be dissolved in 0.5 ml of water. The presence of a deposit in the sample is indicative of the reaction being incomplete. In this case, hydrolysis should be continued for another hour.

On completing the hydrolysis, activated charcoal is added to a yellowish brown solution, which is boiled for 15 min, being thereafter filtered through a glass fabric.

On having been filtered off from the activated charcoal, the solution is concentrated by evaporation in a porcelain cup on a water bath prior to crystallization.

The solution is cooled, and the deposited salt is filtered off through the glass fabric. The mother liquor is thickened by evaporating, cooled, and filtered off in the manner as described above.

The deposit having been added to the previously produced salt, the whole of it is recrystallized from 500 ml of concentrated hydrochloric acid. Properly purified and dried at a temperature of 80°C, the end product is nonhygroscopic, and its moisture content does not exceed 0.4% in storage.

The melting point of the hydrochloride of β-phenyl-γ-aminobutyric acid is 188°–192°C. The yield of the purified product is 565 g.

Example II

Malonic ester is condensed with β-nitrostyrene taken in the amounts indicated in Example I, while maintaining the reaction temperature at 14°C. 1350 g of the methyl ester of α-carbomethoxy-β-phenyl-γ-nitrobutyric acid are separated. The reduction thereof is carried out in a manner similar to that described in Example I, under a pressure of 20 atm. The yield of the product of the reduction, namely 3-carbomethoxy-4-phenyl-2-pyrrolidone amounts to 771 g.

The hydrolysis of 3-carbomethoxy-4-phenyl-2-pyrrolidone is effected in the same manner resulting in the production of 512 g. of the purified hydrochloride of β-phenyl-γ-aminobutyric acid.

Example III

The methyl ester of α-carbomethoxy-β-phenyl-γ-nitrobutyric acid is reduced under a pressure of 6 atm under the conditions indicated in Example I, yielding 700 g of 3-carbomethoxy-4-phenyl-2-pyrrolidone. Boiling it in hydrochloric acid in a manner as described above, yields 466 g of the hydrochloride of β-phenyl-γ-aminobutyric acid.

What is claimed is:

1. A process for the production of the hydrochloride of β-phenyl-γ-amino-butyric acid of the formula:

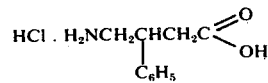

which consists essentially of the steps of condensing malonic ester with β-nitrostyrene resulting in the separation of the methyl ester of α-carbomethoxy-β-phenyl-γ-nitrobutyric acid at a temperature ranging from 0° to 14°C; reducing the ester thus obtained by condensation with hydrogen in the presence of Raney nickel under a pressure of 6 to 30 atm; treating 3-carbomethoxy-4-phenyl-2-pyrrolidone, as formed by the reduction, with hydrochloric acid, and separating the hydrochloride of β-phenyl-γ-aminobutyric acid from the solution.

* * * * *